(12) United States Patent
Miller

(10) Patent No.: US 11,651,840 B2
(45) Date of Patent: May 16, 2023

(54) ACCOUNTING FOR INDUCED FIT EFFECTS

(71) Applicant: Schrödinger, Inc., New York, NY (US)

(72) Inventor: Edward Blake Miller, New York, NY (US)

(73) Assignee: Schrödinger, Inc., New York, NY (US)

( * ) Notice: Subject to any disclaimer, the term of this patent is extended or adjusted under 35 U.S.C. 154(b) by 380 days.

(21) Appl. No.: 16/757,267

(22) PCT Filed: Oct. 18, 2018

(86) PCT No.: PCT/US2018/056494
§ 371 (c)(1),
(2) Date: Apr. 17, 2020

(87) PCT Pub. No.: WO2019/079585
PCT Pub. Date: Apr. 25, 2019

(65) Prior Publication Data
US 2021/0193273 A1    Jun. 24, 2021

Related U.S. Application Data

(60) Provisional application No. 62/574,364, filed on Oct. 19, 2017.

(51) Int. Cl.
*G16C 20/64*        (2019.01)
*G16C 20/40*        (2019.01)
(Continued)

(52) U.S. Cl.
CPC ........... *G16C 20/64* (2019.02); *G16B 15/30* (2019.02); *G16C 20/40* (2019.02); *G16C 20/50* (2019.02)

(58) Field of Classification Search
CPC ........ G16C 20/64; G16C 20/40; G16C 29/50; G16B 15/30; G06F 9/16
(Continued)

(56) References Cited

U.S. PATENT DOCUMENTS 9,914,954 B1 * 3/2018 Caffrey ............... C12Q 1/26
                                                    436/518
2007/0198195 A1    8/2007  Shaw
(Continued)

FOREIGN PATENT DOCUMENTS

JP    2005018447    1/2005
JP    2005508487    3/2005
(Continued)

OTHER PUBLICATIONS

EP Extended European Search Report in European Appln. No. 18868238, dated Dec. 14, 2020, 11 pages.
(Continued)

*Primary Examiner* — Thinh T Nguyen
(74) *Attorney, Agent, or Firm* — Fish & Richardson P.C.

(57) ABSTRACT

A system, device, and method for predicting a docked position of a target ligand in a binding site of a biomolecule is disclosed. The prediction makes use of a template ligand-biomolecule complex structure in order to predict a target ligand-biomolecule complex structure. The system and device contain modules allowing for the prediction of a target-ligand biomolecule complex structure. A preparation module can receive information identifying a target ligand and a template ligand-biomolecule structure. A pharmacophore matcher module can identify common pharmacophores between the template ligand and the target ligand. A docking module can predict a docked ligand position of the target ligand by overlapping the pharmacophore models of the target ligand and template ligand while the template ligand is in the binding site of the biomolecule. A biomolecule modification module can modify the biomolecule to reduce clashes between the docked target ligand and the biomolecule.

15 Claims, 12 Drawing Sheets

(51) Int. Cl.
*G16C 20/50* (2019.01)
*G16B 15/30* (2019.01)

(58) Field of Classification Search
USPC .......................................................... 702/927
See application file for complete search history.

(56) References Cited

U.S. PATENT DOCUMENTS

| 2010/0305152 A1 | 12/2010 | Wang |
| 2012/0053067 A1 | 3/2012 | Mackerell, Jr. et al. |
| 2012/0252687 A1 | 10/2012 | Friesner et al. |

FOREIGN PATENT DOCUMENTS

| WO | WO 2004/075021 | 9/2004 |
| WO | WO 2006081658 | 8/2006 |
| WO | WO 2009/032727 | 3/2009 |
| WO | WO 2008/035729 | 1/2010 |
| WO | WO 2012/028962 | 3/2012 |

OTHER PUBLICATIONS

McCarthy et al., "Pharmacophore-based molecular docking to account for ligand flexibility," Proteins: Structure, Function, and Genetics, May 1, 2003, 51(2):172-188.
Sliwoski et al., "Computational methods in ding discovery," Pharmacological Reviews, Jan. 2014, 66(1):334-395.
Ye et al., "Optimal strategies for virtual screening of induced-fit and flexible target in the 2015 D3R Grand Challenge," Journal of Computer-Aided Molecular Design, Aug. 29, 2016, 30(9):695-706.
Cavasotto et al., "Homology modeling in drug discovery: current trends and applications," Drug Discovery, Jul. 2009, 14(13/14):676-683.
Istvastono et al., "Molecular determinants of ligand binding modes in the histamine H4 receptor: linking ligand-based 3D-DSAR models to in silico guided receptor mutagenesis studies," Journal of Medical Chemistry, Nov. 7, 2011, 54(23):8136-8147.
PCT International Preliminary Report on Patentability in International Appln. No. PCT/US2018/056494, dated Apr. 21, 2020, 10 pages.
PCT International Search Report and Written Opinion in International Appln. No. PCT/US2018/056494, dated Jan. 3, 2019, 11 pages.
Sherman et al., "Novel procedure for modeling ligand/receptor induced fit effects," J Med. Chem., Jan. 2006, 49(2):534-553.

\* cited by examiner

ACCOUNTING FOR INDUCED FIT EFFECTS

TECHNICAL FIELD

This application relates generally to using a computer to assist in predicting a docked position of a target ligand in a binding site of a biomolecule, and relates more specifically to using a computer to assist in predicting a docked position of a target ligand in a binding site of a biomolecule that is capable of undergoing an induced fit.

BACKGROUND

Biomolecules often serve particular functions and the ability to modulate the functionality of a biomolecule can be useful for treating diseases and for engineering industrial biomolecular applications. The functionality of a biomolecule is sometimes modulated by whether and how one or more ligands are bound to the biomolecule. Biomolecules often have regions (e.g., an "active site") where one or more ligands can bind to the biomolecule and thereby modulate the functionality of the biomolecule. For example, competitive antagonists are compounds that can bind to an active site in a biomolecule, thereby inhibiting the natural ligand from binding. Competitive antagonists prevent a biomolecule from performing its biological function, since the biological function requires the natural ligand to be bound in the active site. Similarly, non-competitive antagonists also prevent a biomolecule from performing its biological function, but do so by binding to the biomolecule and changing the biomolecule in some way (such as by changing its three-dimensional conformational ensemble) so that the biomolecule can no longer perform its biological function (e.g., changing the biomolecule's conformation such that it can no longer accommodate the binding of the natural ligand). In contrast to antagonists, an agonist can bind to a biomolecule and activate a particular function of the biomolecule (rather than inhibit the function).

When a ligand binds to a biomolecule, it is useful to know the three-dimensional structure of the ligand-biomolecule complex (the structure of both the ligand and the biomolecule when the ligand is bound to the biomolecule). The three-dimensional structure can provide information about which interactions between the ligand and the biomolecule are important for binding, thereby informing rational drug design. The three-dimensional structure can also be used to calculate the free energy of binding. Unfortunately, it is sometimes difficult to predict the three-dimensional structure of a ligand-biomolecule complex, especially when the biomolecule undergoes an induced fit effect.

SUMMARY

One aspect features a method for predicting a docked position of a target ligand in a binding site of a biomolecule. The method involves receiving a template ligand-biomolecule structure that has a template ligand docked in the binding site of the biomolecule and comparing a pharmacophore model of the template ligand to a pharmacophore model of the target ligand. The pharmacophore model of the target ligand is overlapped with the pharmacophore model of the template ligand while the template ligand is in the binding site of the biomolecule. A docked position is predicted for the target ligand in the binding site of the biomolecule based on a position of the pharmacophore model of the target ligand when overlapped with the pharmacophore model of the template ligand.

Another aspect features a computer system that has at least one processor, a preparation module, a pharmacophore matcher module, and a docking module. The preparation module is stored in memory and coupled to at least one processor, and is programmed to receive information identifying a target ligand and a template ligand-biomolecule structure comprising a template ligand and a biomolecule. The pharmacophore matcher module is stored in memory and coupled to at least one processor, and is programmed to identify a pharmacophore match between the template ligand and the target ligand by comparing the pharmacophore model of the template ligand to the pharmacophore model of the target ligand. The docking module is stored in memory and coupled to at least one processor, and is programmed to predict a docked ligand position of the target ligand in the template ligand-biomolecule structure by overlapping the pharmacophore model of the target ligand with the pharmacophore model of the template ligand while the template ligand is in the binding site of the biomolecule.

Another aspect features a non-transitory computer readable storage medium having a computer readable program that when executed on a computer causes the computer to predict a docked position of a target ligand in a binding site of a biomolecule. Making the prediction as to the docked position of the target ligand in the binding site of the biomolecule involves performing various steps. One step involves receiving information identifying the target ligand and a template ligand-biomolecule structure, using a preparation module stored in memory and coupled to at least one processor. The template ligand-biomolecule structure has a template ligand docked in the binding site of the biomolecule. Another step involves identifying a pharmacophore match between the template ligand and the target ligand, using a pharmacophore matcher module stored in memory and coupled to at least one processor. The process of identifying the pharmacophore match involves comparing a pharmacophore model of the template ligand to a pharmacophore model of the target ligand. Another step involves predicting a docked ligand position of the target ligand, using a docking module stored in memory and coupled to at least one processor. The docking module predicts the docked position of the target ligand in the binding site of the biomolecule based on a position of the pharmacophore model of the target ligand when overlapped with the pharmacophore model of the template ligand while the template ligand is in the binding site of the biomolecule.

In some implementations, the target ligand is selected from a plurality of ligand candidates, each of the ligand candidates being different from the template ligand. Selecting the target ligand involves comparing the pharmacophore model of the template ligand to a pharmacophore model of each respective one of the plurality of ligand candidates.

In some implementations, a plurality of template ligand-biomolecule structures is received, each template ligand-biomolecule structure having a different template ligand docked in the binding site of the biomolecule. The pharmacophore model of the template ligand is generated by combining information from each of the template ligands from the plurality of template ligand-biomolecule structures.

In some implementations, the target ligand has more than one structural conformation in its unbound state, and the docked position of the target ligand in the binding site of the biomolecule is predicted by enumerating a set of potential target ligand conformations and overlapping a respective pharmacophore model of the target ligand for each of the potential target ligand conformations with the pharmacophore model of the template ligand while the template ligand is in the binding site of the biomolecule.

In some implementations, predicting the docked position of the target ligand in the binding site of the biomolecule involves ignoring at least one clash between the target ligand conformation's atomic coordinates and the biomolecule's atomic coordinates. In some instances of these implementations, for each target ligand conformation, the atomic coordinates of the biomolecule are modified to reduce clashes between the docked target ligand conformation's atomic coordinates and the biomolecule's atomic coordinates, thereby creating an altered ligand-biomolecule structure comprising the docked target ligand and an altered biomolecule.

In some implementations, a re-docked position of each target ligand conformation is predicted by predicting each target ligand conformation's position in the binding site of the altered biomolecule. For each target ligand conformation, the atomic coordinates of the altered biomolecule are modified to reduce clashes between the atomic coordinates of the target ligand conformation's re-docked position and the atomic coordinates of the altered biomolecule, thereby creating a re-altered ligand-biomolecule structure comprising a re-docked target ligand and a re-altered biomolecule.

In some implementations, each altered and re-altered ligand-biomolecule structure is ranked using a scoring function. In some instances of these implementations, a subset of high-ranking target ligands corresponding to target ligands having a threshold value for an empirical activity is identified.

DETAILED DESCRIPTION

Figure 7A:
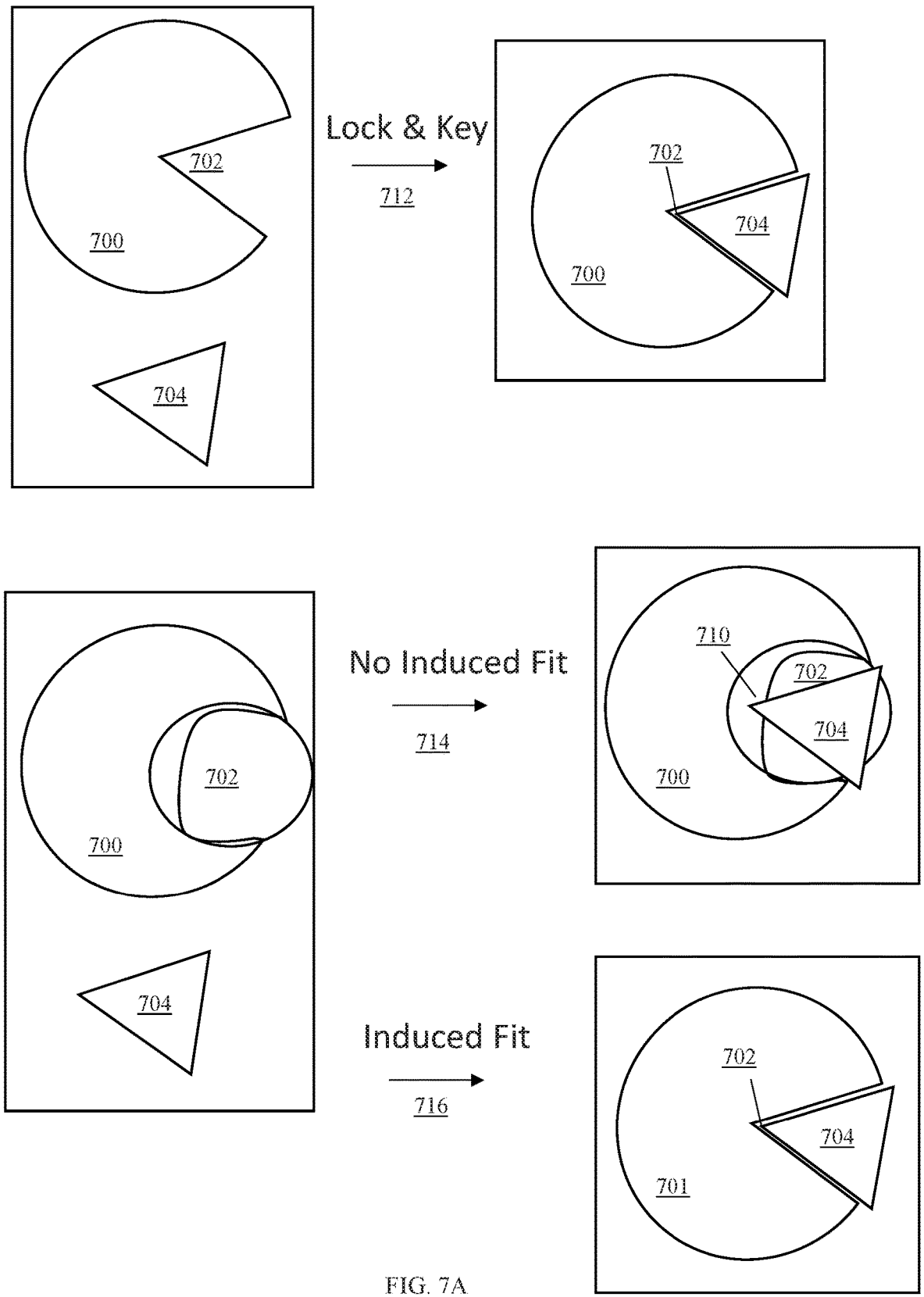
FIG. 7A is a cartoon diagram illustrating the process of a ligand binding to a biomolecule.
Figure 7B:
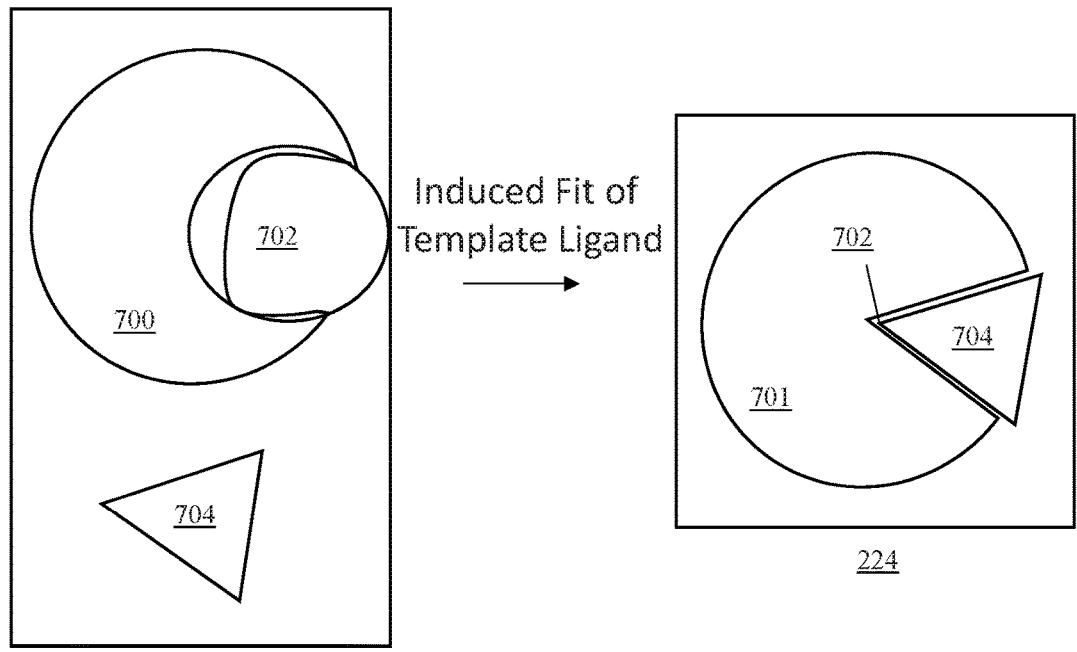
FIG. 7B is a cartoon diagram illustrating the process of induced fit binding for both a template ligand and a target ligand.
Figure 7B:
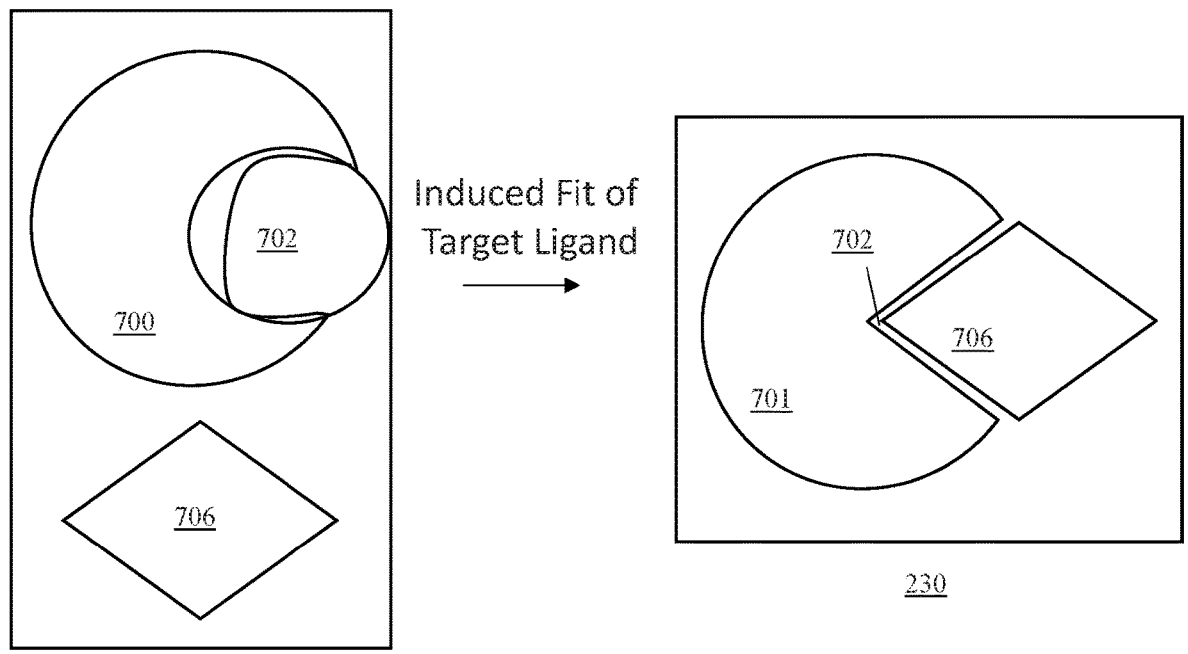

Frequently, scientists and engineers are aware of the structure of a template ligand 704 that binds to a biomolecule 700 (i.e., the structure of a template ligand-biomolecule complex 224), but either know or suspect that a different target ligand 706 also binds to the same biomolecule 700 (see FIG. 7B). In general, scientists and engineers may be interested in the target ligand 706 because it may (i) have higher binding affinity than the template ligand 704, (ii) be more commercially viable than the template ligand 704, (iii) be metabolized in a safer way than the template ligand 704, (iv) not be covered by the same intellectual property rights as the template ligand 704, etc. In such situations, scientists and engineers would like to know the three-dimensional structure of the target ligand 706 when bound to biomolecule 700 because the three-dimensional structure can provide information about which interactions between the target ligand 706 and the biomolecule 700 are important for binding (thereby informing rational drug design). Additionally, the three-dimensional structure can also be used to calculate the free energy of binding of target ligand 706. Computers can help reduce the cost and time involved in obtaining a three-dimensional structure; sometimes, computers are the only viable option because empirical techniques (e.g., x-ray crystallography and NMR) are sometimes unsuccessful at determining a three-dimensional structure, especially when the biomolecule has flexible/floppy regions.

As described herein, the three-dimensional structure of a template ligand 704 bound to a biomolecule 700 can be used to predict the three-dimensional structure of a target ligand 706 bound to the same (or similar) biomolecule 700. Unfortunately, when a ligand binds to a particular biomolecule, the biomolecule does not always keep its original three-dimensional conformation. As shown in FIG. 7A, there are generally two different modes of ligand binding: (i) the "lock and key" mode 712, and (ii) the "induced fit" mode 716. When a ligand's shape and properties complement a biomolecule's shape and physical properties, binding can occur through the "lock and key" mode 712 and the biomolecule may not need to undergo significant conformation changes. However, when a ligand's shape and properties do not complement a biomolecule's shape or physical properties, then binding will occur through the "induced fit" mode 716 and the biomolecule 700 will change its conformation into an altered biomolecule 701 in order to avoid clashes (e.g., clash 710). Consequently, the conformation of biomolecule 700 when bound to template ligand 704 may not accurately represent the conformation of biomolecule 700 when bound to target ligand 706, due to conformational changes associated with the induced fit effect.

Among other advantages, the prediction system and methods disclosed herein describe how to predict conformational changes that result from the induced fit effect. In particular, the system and methods describe how computational methods can be used to predict the three-dimensional structure of a target ligand-biomolecule complex 230 (comprising target ligand 706 bound to biomolecule 701, where biomolecule 701 is biomolecule 700 after undergoing conformational changes), given a template ligand-biomolecule structure 224 (comprising template ligand 704 and biomolecule 700). In some implementations, more than one target ligand 706 is analyzed, and each one is ranked based on a scoring function. The top-ranking target ligands 706 can be chemically synthesized for empirical testing. Another advantage is that in some implementations, the structure of the biomolecule in the predicted ligand-biomolecule complex 230 can be used as a modified biomolecule in rigid-receptor docking and other drug discovery techniques.

Figure 1:
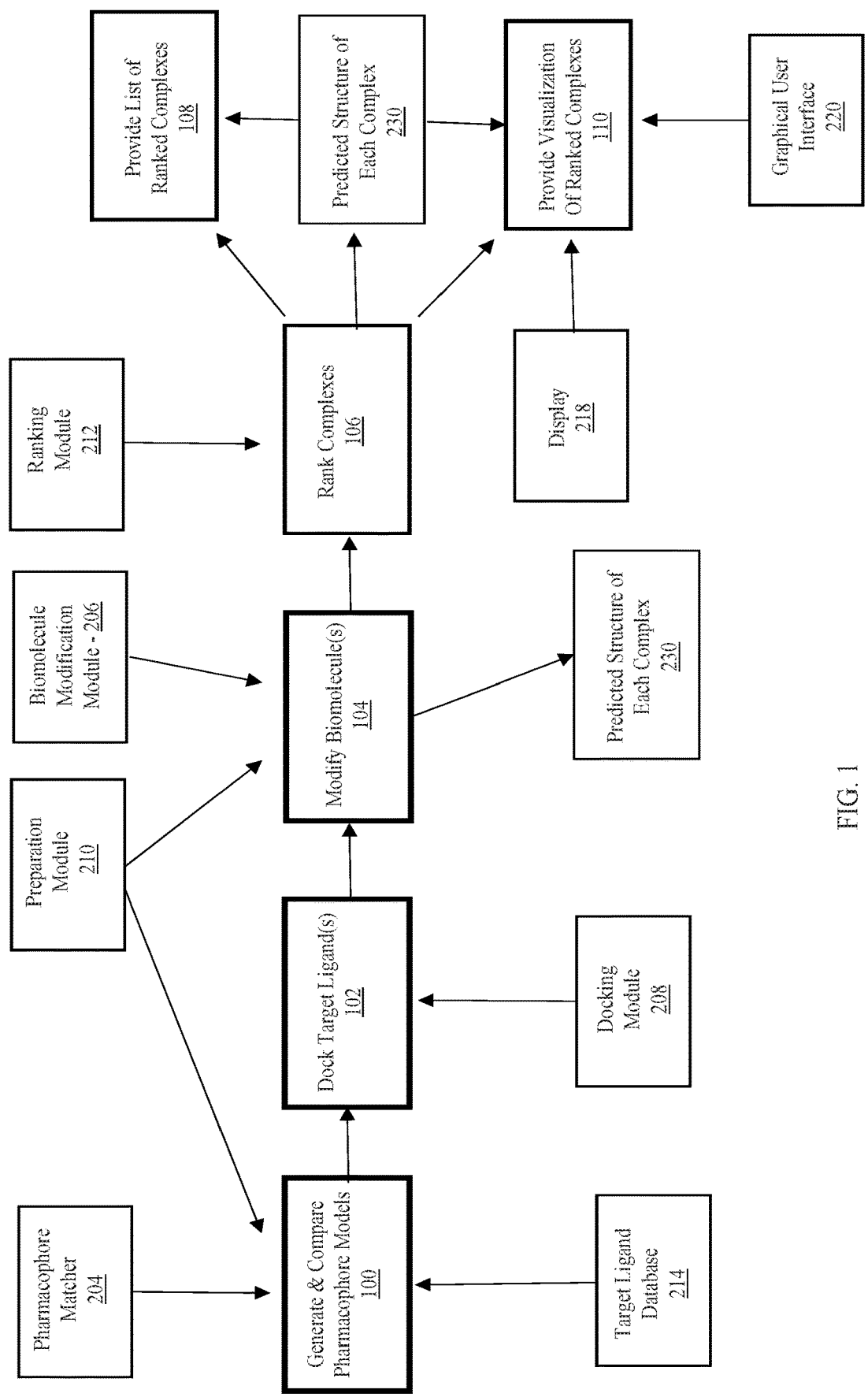
FIG. 1 is a block/flow diagram showing a method of predicting a docked position of a target ligand in a binding site of a biomolecule.

FIG. 1 shows a block/flow diagram illustratively depicting one embodiment of a method for predicting a docked position of a target ligand 706 in a binding site of a biomolecule 700, where blocks 100 through 110 (outlined in bold) represent steps of the method. The prediction system 200 shown in FIG. 2 can implement steps of the method shown in FIG. 1.

Figure 2:
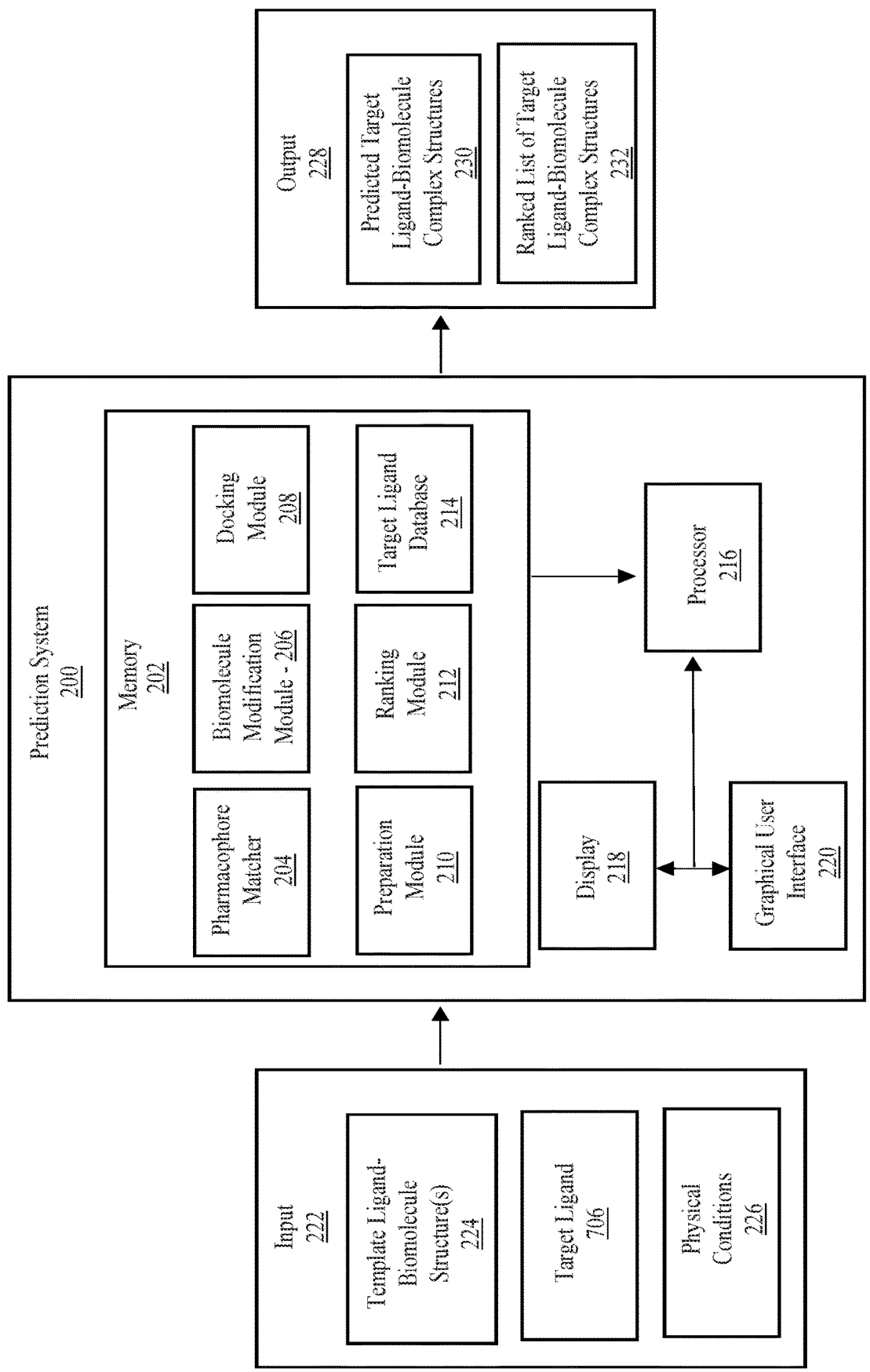
FIG. 2 is a block diagram showing a prediction system for predicting a docked position of a target ligand in a binding site of a biomolecule.

Before performing the first step 100 of the method shown in FIG. 1, the prediction system 200 (see FIG. 2) receives input 222 from a user or in an automated fashion (e.g., automatically downloading the input 222 from a server). Referring to FIG. 2, the input 222 includes at least one three-dimensional atomic structure of the template ligand-biomolecule complex 224 and also includes information identifying at least one target ligand 706. The template ligand-biomolecule complex 224 includes a biomolecule 700 and a template ligand 704 that is bound to the biomolecule 700. The template ligand 704 can be bound to binding site 702 (e.g., an active site or allosteric site) of the biomolecule 700. The at least one template ligand-biomolecule structure 224 can be obtained empirically (e.g., using NMR or x-ray crystallography) or computationally (e.g., using a biomolecule structure prediction system, such as CHARMM, AMBER, or GROMACS). The template ligand-biomolecule complex 224 can be an incomplete structure—e.g., some empirical techniques are incapable of resolving the myriad three-dimensional structures adopted by floppy/flexible regions of a biomolecule. In these situations, the unresolved regions of the incomplete template ligand-biomolecule complex 224 can be resolved using the molecule dynamics module 504 of the prediction system 200, or using any other biomolecular structure prediction module or system. The ligand-biomolecule complex 224 can also be incomplete for other reasons, e.g., because a contiguous set of atomic coordinates may be undesirable or not needed, such as in the case where distant atoms not significantly involved in the complexation may be ignored to save computational resources, or in the case where regions of the template ligand make contacts with the biomolecule and such contacts are unlikely to be shared by the target ligand. The prediction system 200 can also receive other input, such as information about physical conditions 226 (e.g., pH, temperature, and salt concentration).

The target ligand 706 is sometimes provided as input 222 by a user. For example, a user may know that a particular ligand (different from the template ligand 704) binds more strongly to biomolecule 700 than the template ligand 704 or has better ADME properties than the template ligand 704. In such a case, the known ligand can be the target ligand 706 that is provided as input 222 by a user seeking to know the three-dimensional structure of the target ligand 706 when bound to a biomolecule 700. Alternatively, the target ligand 706 can be selected from a plurality of ligand candidates stored in a target ligand database 214.

Referring to FIGS. 1-2, the first step 100 of the method shown in FIG. 1 involves comparing at least one pharmacophore model of the template ligand 704 with at least one pharmacophore model of the target ligand 706. Pharmacophore generator 300 can be used to identify pharmacophores of different types (e.g., aromatic type, hydrophobic type, etc.). A pharmacophore model comprises one or more pharmacophores and can include information about the relative location of the pharmacophores and the directionality of the pharmacophores (when applicable).

The pharmacophore models used in step 100 can either be generated by the prediction system 200 (e.g., using pharmacophore generator 300) or provided as input 222 to the prediction system 200. The pharmacophore models used in step 100 need not be generated from the same source (e.g., the pharmacophore model of the target ligand 706 can be provided as input 222, while the pharmacophore model of the template ligand 704 can be generated by the prediction system 200).

Figure 8A:
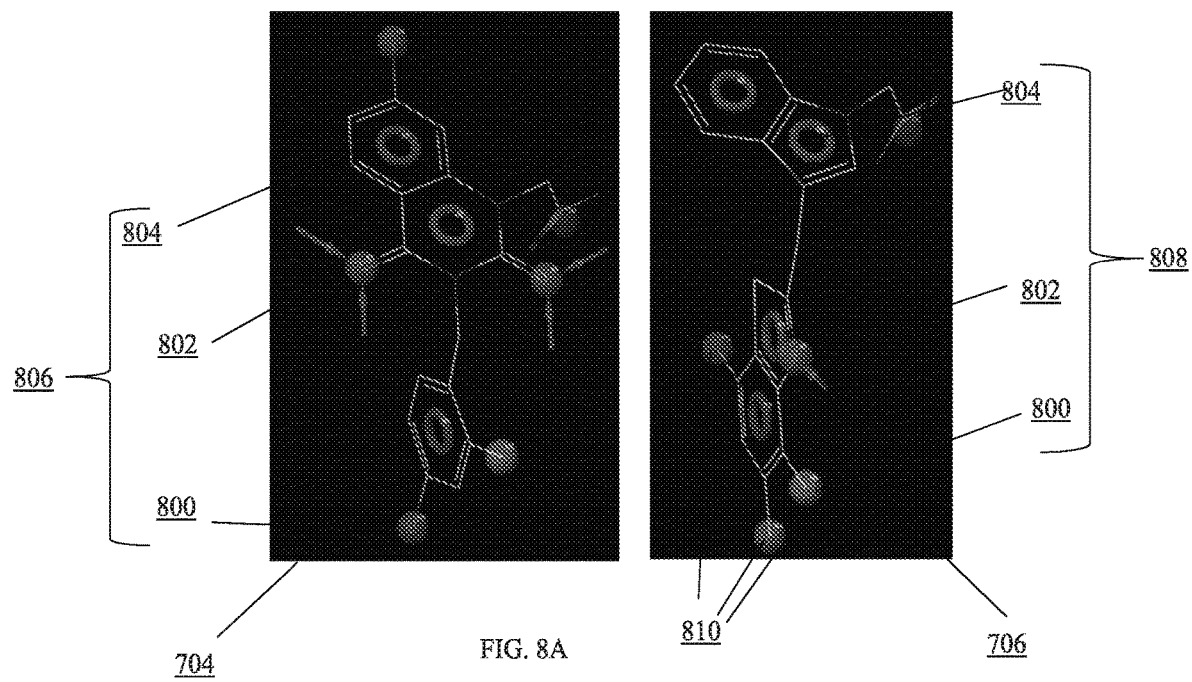
FIG. 8A illustrates a pharmacophore model for a template ligand and a target ligand.

FIG. 8 illustrates example pharmacophore models for a specific template ligand 704 and a specific target ligand 706. As shown in FIG. 8A, the template ligand 704 has nine distinct pharmacophores, comprising three types: aromatic groups 804 represented by orange rings, hydrogen-bond acceptors 802 represented by red spheres, and hydrophobic groups 800 represented by green spheres. Together, all nine pharmacophores, or a subset thereof, can make up the pharmacophore model 806 for template ligand 704. Similarly, the target ligand 706 also has nine distinct pharmacophores, comprising the same three types. Together, all nine pharmacophores, or a subset thereof, can make up the pharmacophore model 808 of target ligand 706. The template ligand 704 and target ligand 706 may, but need not, have the same number of pharmacophores. The pharmacophore generator 300 (see FIG. 3) can be used to generate pharmacophores like those in FIG. 8. For example, the pharmacophore generator 300 can have an aromatic detector 310 to detect aromatic groups 804, a hydrophobe detector 312 to detect hydrophobic groups 800, and a hydrogen-bond acceptor detector 318 to detect hydrogen bond acceptors 802. A pharmacophore model can comprise more than one instance of a pharmacophore type, e.g., pharmacophore type 800 (hydrophobic groups represented by green spheres in FIGS. 8A-9) has three pharmacophore instances 810 in target ligand 706, all of which could form part of a pharmacophore model of the target ligand 706.

If not provided as input 222, pharmacophore models like those shown in FIG. 8 can be generated by pharmacophore generator 300 using a number of different techniques. Each pharmacophore type (e.g., aromatic groups 804, hydrogen-bond acceptors 802, and hydrophobic groups 800) within a pharmacophore model can be identified using pre-determined criteria. For example, instances of a hydrogen bond acceptor type 802 can be identified by searching for any surface-accessible atom that has one or more donatable lone electron pairs. Similarly, instances of a hydrogen bond donor type (detected by hydrogen bond donor detector 320) can be identified by searching for donatable hydrogen atoms. As another example, instances for a hydrophobic group type 800 can be identified by searching for rings, isopropyl groups, t-butyl groups, various halogenated moieties, and chains as long as four carbons (using this scheme for identifying hydrophobic group instances, chains of more than four carbons can be divided up into smaller fragments having between two to four carbons).

Once every instance of a pharmacophore type is identified (e.g., instances 810 of the hydrophobic group type 800) in a molecule, pharmacophore generator 300 can be used to create a more detailed pharmacophore model by characterizing each of the pharmacophore instances based on their location within the molecule and their directionality (if applicable). There are various methods for identifying the location of a particular instance of a pharmacophore type. As one example, the location of an instance of a hydrophobic group type 800 can be defined as the weighted average of the positions of the non-hydrogen atoms in the identified instance. As another example, the location of negative and positive ionizable sites (identified using negative ionizable detector 316 and positive ionizable detector 314, respectively) can be defined as a single point located on a formally charged atom, or at the centroid of a group of atoms over which the ionic charge is shared. As yet another example, the location of an instance of an aromatic type 804 can be defined as the centroid of the aromatic ring.

Various methods also exist for identifying the directionality of particular instances of pharmacophore types. Whether a pharmacophore type has directionality can be a pre-determined setting of pharmacophore generator 300. For example, the hydrophobic group type 800 can be deemed to have no directionality component because hydrophobic interactions are frequently directionless, while the hydrogen bond donor/acceptor types (e.g., hydrogen-bond acceptors 802) can be deemed to have directionality because an interaction between this type and a biomolecule 700 frequently requires directional polar interactions along the hydrogen bond axis. Directionality of a type can be represented as a vector, as symbolized by the arrows 812 associated with the hydrogen-bond acceptor type 802 in FIG. 8B. As another example of how directionality can be associated with a particular pharmacophore type, the directionality of the aromatic group type 804 can be defined as a two-headed vector normal to the plane of the aromatic ring (to correctly describe ring-stacking interactions).

Figure 9:
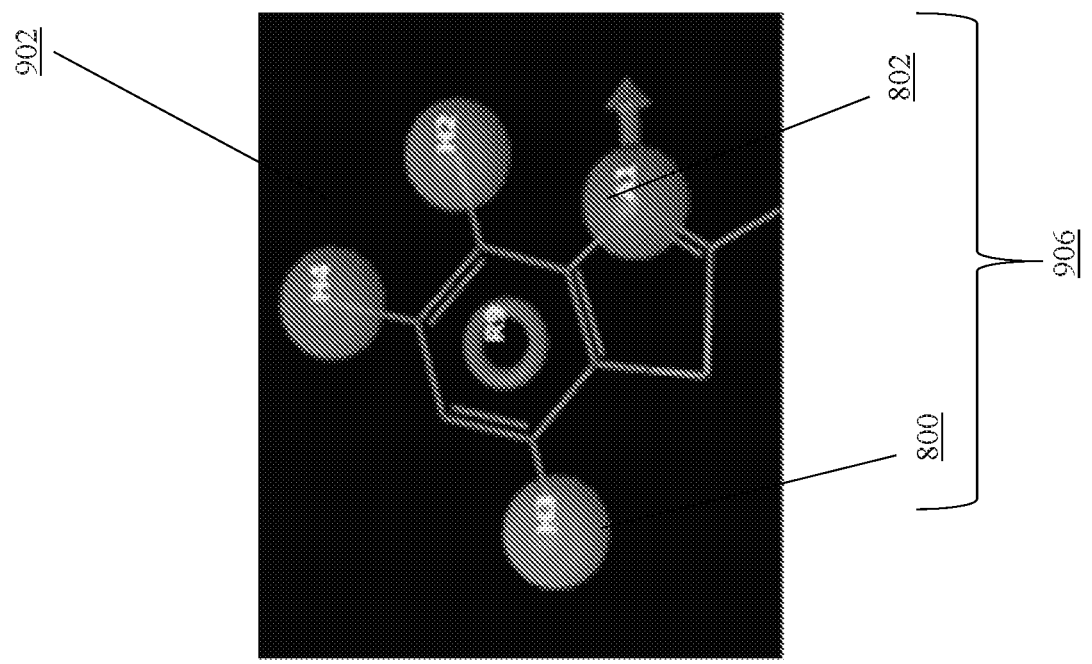
FIG. 9 illustrates an example of how multiple pharmacophore models can be created for a single ligand.
Figure 9:
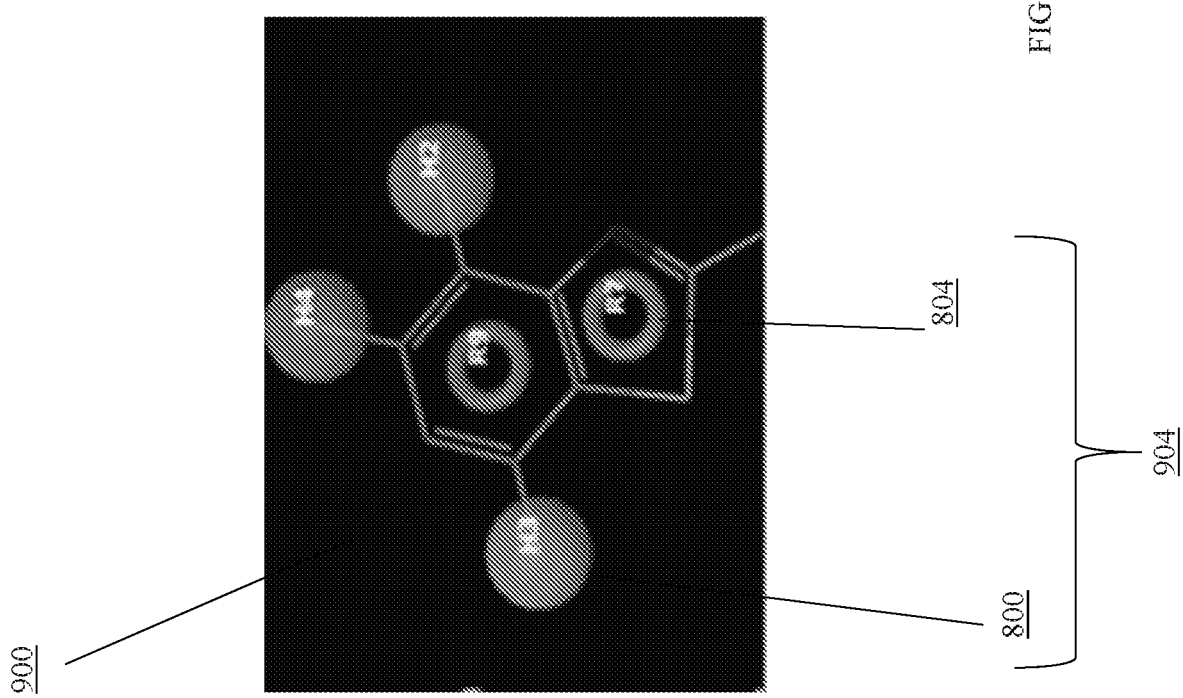

Referring to FIG. 9, more than one pharmacophore model can be generated for any particular molecule. For example, the two snapshots shown in FIG. 9 (snapshot 900 and snapshot 902) illustrate the same fused-ring molecule, but with different pharmacophore models. The difference between the pharmacophore model shown in snapshot 900 and the pharmacophore model shown in snapshot 902 is that in snapshot 900, the 5-membered ring is represented as an aromatic pharmacophore type 804, while in snapshot 902 the 5-membered ring is represented as having a hydrogen bond acceptor pharmacophore type 802. Both pharmacophore models (model 904 for snapshot 900, and model 906 for snapshot 902) are acceptable models. Another situation when more than one pharmacophore model can be generated for any particular molecule is the case where a molecule exists in multiple different three-dimensional conformation, e.g., when the target ligand 706 has a cyclohexane ringstructure that can exist in either a chair conformation or a boat conformation. When the target ligand 706 has more than one structural conformation in its unbound state, a pharmacophore model 808 can be created for each conformation of the target ligand 706, and the method shown in FIG. 1 can be performed on each conformation of the target ligand 706.

A pharmacophore model can be based on pharmacophores perceived in more than just one molecule. For example, more than one template ligand-biomolecule structure 224 can be received as input 222. When more than one template ligand-biomolecule structure 224 is received, each of the structures 224 can have a different template ligand 704 docked in the binding site 702 of the biomolecule 700. In such cases, step 100 can involve generating a pharmacophore model 806 of the template ligands 704 by combining information from each of the respective template ligands 704 from the plurality of template ligand-biomolecule structures 224. Pharmacophores common to each of the respective template ligands 704 can be used to create a combined pharmacophore model. Additionally, more than one pharmacophore model 806 can be generated from the plurality of template ligands 704. In such cases, if the template ligand-biomolecule structures 224 have known binding affinities of the associated template ligands 704, then the binding affinities can be provided as input 222 and pharmacophore models of template ligands 704 can be given greater weight in the pharmacophore model if they belong to a template ligand 704 with higher binding affinity.

Figure 8B:
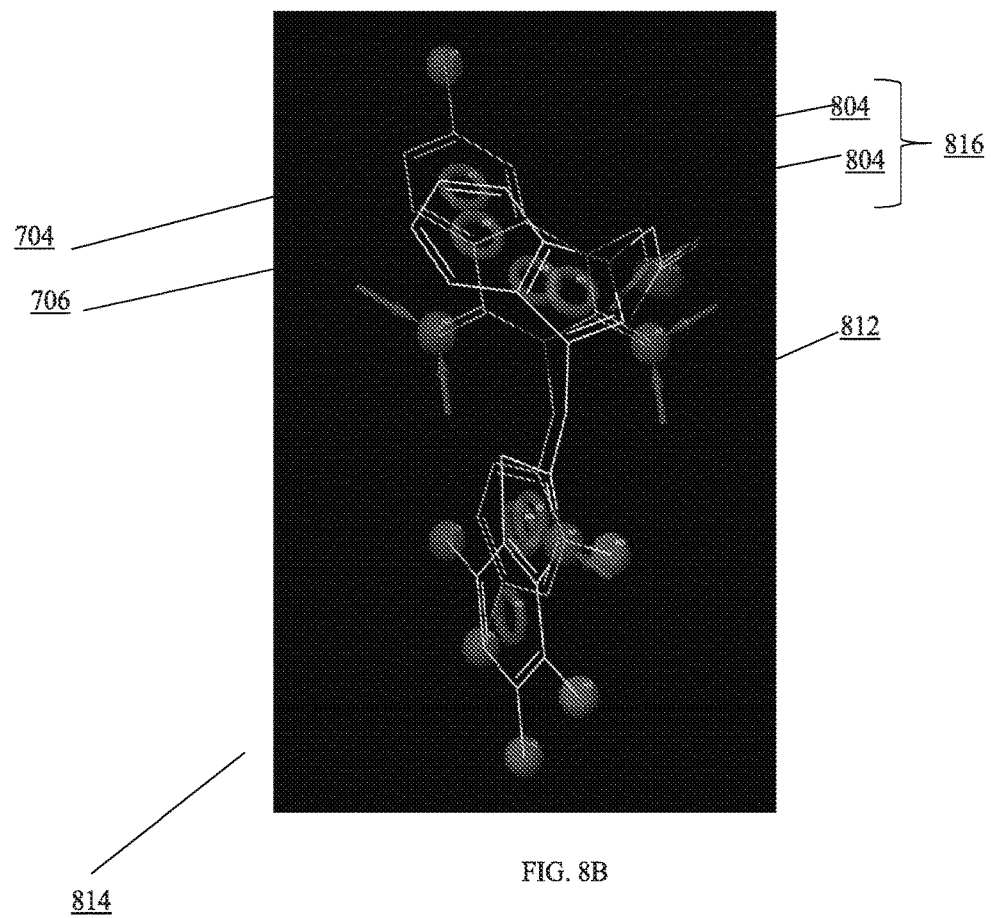
FIG. 8B illustrates an overlap between the pharmacophore model of the template ligand and the target ligand.

Once at least one pharmacophore model 806 of the template ligand 704 and at least one pharmacophore model 808 of the target ligand 706 has been generated by pharmacophore generator 300 (or received as input 222), step 100 of FIG. 1 next involves comparing the at least one pharmacophore model 806 of the template ligand 704 with the at least one pharmacophore model 808 of the target ligand 706. The objective of the comparison is to identify pharmacophore types common to both the pharmacophore model 806 of the template ligand 704 and the pharmacophore model 808 of the target ligand 706. The pharmacophore match detector 306 can be used to identify common pharmacophores between the template ligand 704 and target ligand 706 (e.g., FIG. 8B shows a pharmacophore match 816 where the aromatic group type 804 is found in both the template ligand 704 and the target ligand 706).

Various techniques can be used for comparing pharmacophore models, with the underlying goal being the identification of pharmacophores common to both molecules being compared (e.g., common to both template ligand 704 and target ligand 706), and especially the identification of pharmacophores with similar topological arrangements and directionality. In general, the pharmacophore types common to both the template ligand 704 and the target ligand 706 can be superimposed. More than one superimposed option may be possible (e.g., when more than one instance 810 of a particular pharmacophore type is present in the template ligand 704 or the target ligand 706 or both), in which case various techniques can be used to rank the superimposition options. For example, the RMSD between the superimposed common pharmacophores can be calculated—superimposition options with lower RMSD can be more highly ranked, and the highest-ranking superimposition option (e.g., superimposition option 814 shown in FIG. 8B) can be chosen first for the implementation of steps 102-110 in FIG. 1. The output of step 100 can be at least one superimposition of the pharmacophore model of target ligand 706 and the pharmacophore model of template ligand 704 (e.g., superimposition 814).

When a target ligand 706 and/or a template ligand 704 has more than one potential pharmacophore model, each pharmacophore model of the template target ligand 704 is compared (step 100) to each pharmacophore model of the target ligand 706. Such a comparison can be done serially or in parallel using the pharmacophore match detector 306.

Figure 10:
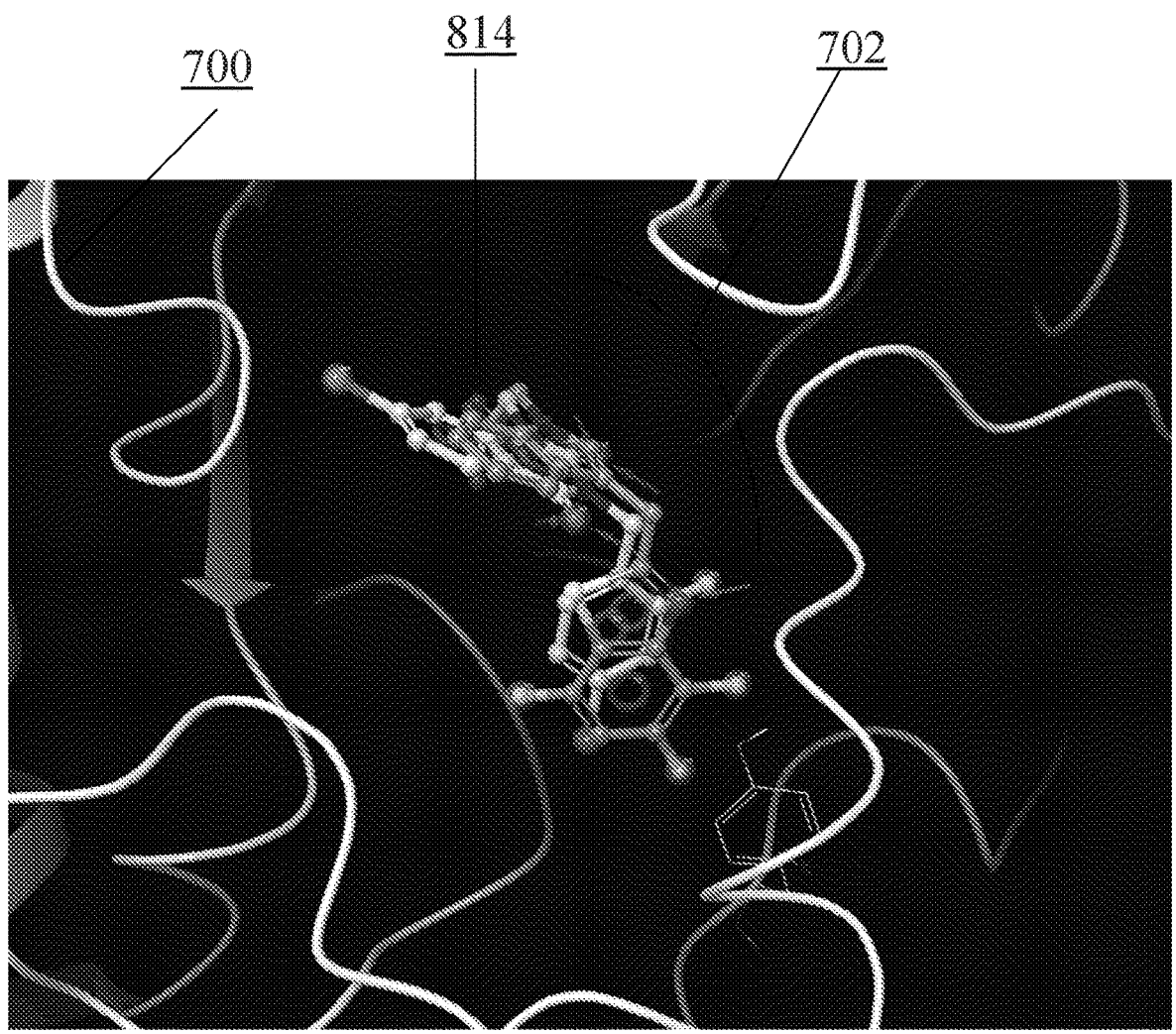
FIG. 10 illustrates an overlap between the template ligand and the target ligand illustrated in FIG. 9 B while the template ligand is in the active site of a biomolecule.

The next step shown in FIG. 1 is step 102, which involves docking the target ligand 706 into a binding site of biomolecule 700 (e.g., into the active site 702 of the biomolecule 700). Step 102 can be accomplished using docking module 208. Docking the target ligand 706 into the active site 702 involves overlapping the pharmacophore model 808 of the target ligand 706 with the pharmacophore model 806 of the template ligand 704 while the template ligand 704 is in the binding site 702 of the biomolecule 700. Such an overlap can be achieved by selecting the highest-ranking superimposition option (e.g., superimposition option 814) resulting from the comparison in step 100. The highest-ranking superimposition option (e.g., superimposition option 814) can then be overlapped/superimposed in the active site 702 of the biomolecule 700, as shown in FIG. 10. Other lower-ranking superimposition options can also be docked, either serially or in parallel to the highest-ranking option.

Step 102 may result in energetically unfavorable interactions ("clashes") between the atoms in the target ligand 706 and the biomolecule 700. Clashes (e.g., clash 710 shown in FIG. 7A) indicate which portions of the biomolecule 700 are likely to undergo an induced fit effect. Importantly, in the methods disclosed here, some or all of such clashes can be ignored during step 102. While it is acceptable to ignore all clashes in some implementations, in other implementations some clashes may be deemed too severe to ignore. Whether a clash is deemed too severe to ignore can be determined by analyzing pre-set criteria (e.g., default criteria of docking module 208, or criteria provided as user input 222). For example, in some implementations, a clash between an atom of target ligand 706 and a backbone atom of biomolecule 700 (as opposed to a side-chain atom of biomolecule 700) may be deemed too severe to ignore. If a clash is deemed too severe to ignore in the pre-set criteria, then the method shown in FIG. 1 can either be terminated at step 102 for the particular superimposition option being analyzed, or the prediction system 200 can output a message to the user indicating that the particular superimposition option being analyzed may result in highly unfavorable interactions requiring major modifications of the biomolecule 700.

The next step shown in FIG. 1 is step 104, which involves modifying the biomolecule 700 in response to the presence of the target ligand 706 (e.g., in response to clashes between the target ligand 706 and the biomolecule 700). Step 104 models the "induced fit" effect. Biomolecule modification module 206 can be used to accomplish step 104. When performing step 104, the atoms of the template ligand 704 can be deleted or ignored (i.e., treated as "dummy" atoms). There are many techniques by which biomolecule 700 can undergo conformational modification (i.e., the movement of the atomic coordinates of the biomolecule 700) in response to the presence of target ligand 706. For example, clashes 710 can be resolved using minimizer 404 to perform molecular mechanics minimization of the clashing atoms in the biomolecule 700 while restraining the atoms of the target ligand 706 (e.g., using a harmonic restraint). For better sampling of conformational space, molecular mechanics minimization can be followed by molecular dynamics simulation using molecular dynamics module 504. As another example, clashes 710 can be resolved by Monte Carlo conformational searches to explore non-clashing positions of the side-chains of biomolecule 700 (e.g., rotamer optimization) using conformation explorer 502.

Other modifications besides conformational modifications are also possible. For example, if biomolecule 700 is a protein, then clashes 710 that are between target ligand 706 and specific sidechains of biomolecule 700 may be resolved by computationally mutating the clashing sidechains, e.g., by truncating the clashing sidechains of biomolecule 700 to alanine (alanine is a relatively small amino acid that is less likely to sterically clash with a target ligand 706). The clashing sidechains of biomolecule 700 can also be computationally mutated to residues larger than alanine but smaller than the clashing residues in biomolecule 700, e.g., a leucine could be mutated to a valine, a tyrosine or tryptophan could be mutated to phenylalanine, a glutamine could be mutated to asparagine, a glutamic acid could be mutated to an aspartic acid, etc.

One or all of the above-mentioned techniques can be used to resolve clashes 710 and ultimately achieve an induced fit effect. By modifying the biomolecule 700, an altered biomolecule 701 is created that has a different three-dimensional structure (and possibly a different chemical make-up) than the biomolecule 700. The output of step 104 is the predicted structure of the target ligand-biomolecule complex 230, which comprises target ligand 706 and altered biomolecule 701.

The next step shown in FIG. 1 is step 106, which involves ranking the target ligand-biomolecule complexes 230 that are output from step 104. Each complex 230 output from step 104 comprises a target ligand 706 and altered biomolecule 701. The complexes 230 can be ranked according to any number of scoring functions, which can be used to calculate the affinity between the target ligand 706 and altered biomolecule 701. Scoring functions can generally be force-field-based (using classical molecular mechanics energy functions), knowledge-based (using a potential created from statistical probability distributions of interatomic distances in known ligand-biomolecule complexes), and/or empirical-based (i.e., weighting structural moieties based on experimental binding affinities from a training set of known biomolecule-ligand complexes).

When some predicted target ligand-biomolecule complexes 230 are resolved by mutational modification using mutator 506, but others are resolved by only conformational modification (e.g., using only minimizer 404), all complexes 230 can be ranked together using a scoring function that is a function of interactions between the target ligand 706 and altered biomolecule 701. Such mutated sidechains can be restored to the original sidechain (by using mutator 506 and then preparation module 210 for minimization and/or sampling) after the modification step 104 of the process shown in FIG. 1. The mutated residues can be restored to the original sidechain either before or after the ranking step 106. All complexes can be scored together in ranking step 106 under the assumption that mutating non-interacting residues (i.e., those residues that do not form significant contacts with the biomolecule 700) will not affect scoring, but mutating interacting residues (e.g., residues forming a salt bridge with biomolecule 700, residues involved in pi-stacking with biomolecule 700, etc.) would negatively impact scoring since those interacting residues are presumably key for binding.

In some implementations, a subset of the top-ranking complexes listed in step 108 of FIG. 1 can be synthesized for empirical structural analysis (e.g., using x-ray crystallography or NMR, etc.) or empirical activity analysis (e.g., using calorimetry, electrophoresis, ELISA, fluorescence changes, etc.). The subset of top-ranking complexes listed in step 108 can be chosen using a pre-determined cut-off, e.g., the top 10%, which can be ultimately provided as a list of ranked complexes 232. The pre-determined cut-off could also represent a threshold value for an empirical activity, where the threshold value can be specified as user input 222 (e.g., activity in the nanomolar range or better). When using a threshold value for an empirical activity as the pre-determined cut-off, it is important that step 106 uses a scoring function that is capable of closely approximating the binding free energy $\Delta G$ of a target ligand 706, in order to accurately derive a dissociation constant $K_d$ (representing the activity) for each target ligand 706. The dissociation constant associated with the binding of a target ligand 706 can be calculated using the following equation: $\Delta G = -k \, T \ln K_d$, where $\Delta G$ is the binding free energy, k is the Boltzmann constant, T is the temperature, and $K_d$ is the dissociation constant. Based on the calculated dissociation constant $K_d$, a subset of top-ranking complexes listed in step 108 can be created (e.g., a subset having a predicted activity in the nanomolar range or better) and provided as a list of ranked complexes 232.

The output 228 of the method shown in FIG. 1 includes the structure of each target ligand-biomolecule complex 230 (where the target ligand-biomolecule complex 230 comprises the target ligand 706 and the altered biomolecule 701), which can be used to create a list of ranked complexes 232 (step 108) and/or used for the visualization of ranked complexes (step 110). Whether a list of ranked complexes 232 (step 108) or a visualization of them (step 110) is produced (or both), the output can include information about atomic coordinates of each of the three-dimensional structures of the target ligand-biomolecule complex 230. The output 228 may be visualized on one or more displays 218 that are coupled to one or more graphical user interfaces 220. For example, the three-dimensional structures of the ranked complexes can be shown on display 218 and the three-dimensional structures can be manipulated and modified by a user via graphical user interface 220.

In some implementations, steps 102-110 can be repeated. For example, step 102 can be performed on the list of ranked complexes 108 in order to predict a re-docked position of each target ligand 706 (including all three-dimensional conformations of each target ligand 706) by predicting each target ligand's 706 position in the binding site 702 of the altered biomolecule 701. Alternatively, step 102 can be performed on the predicted complexes 230 that were output from modification step 104 (without ranking those complexes 230). Instead of using pharmacophore overlapper 602 to predict the target ligand's 706 re-docked position in altered biomolecule 701, re-docking can be done by optimizing interactions between the target ligand 706 and the active site 702 of biomolecule 701 (e.g., optimizing hydrogen bonding interactions, salt-bridges, hydrophobic interactions, etc.), using the interaction optimizer 604 of docking module 208. Given a re-docked position, steps 104-110 can be performed on the re-docked target ligand 706 and altered biomolecule 701 (yielding the structure of a target ligand 706 bound to a re-altered version of altered biomolecule 701). In cases where clashing residues were mutated during step 104, the original residues can be restored using mutator 506, before repeating step 104. In some implementations, this re-docking procedure can lead to more accurate structural predictions of the target ligand-biomolecule complex 230. When steps 102-110 are repeated, step 106 (involving ranking of the predicted structure of each target ligand-biomolecule complex 230) can comprise ranking all target ligand-biomolecule complexes 230, including those that have an altered biomolecule 701 and those that have a re-altered biomolecule structure (where the re-altered biomolecule structure is the result of repeating steps 102-104 in FIG. 1), using a scoring function.

A number of embodiments of the claimed methods have been described. Nevertheless, it will be understood that various modifications can be made without departing from the spirit and scope of the claims. For example, greater or fewer steps can be performed than are shown in FIG. 1, and the steps of FIG. 1 do not necessarily need to be performed in a particular order. For instance, the pharmacophore models generated in step 100 could first be visualized using display 218 and graphical user interface 220 before actually being compared using pharmacophore matcher 204. As another example, in cases of only one template ligand-biomolecule structure 224 and only one fairly inflexible target ligand 706, the step of ranking complexes 230 (step 106) may not be performed.

Referring to FIG. 2, a computer prediction system 200 can be used for predicting a target ligand-biomolecule structure 230 after receiving as input one or more template ligand-biomolecule complex structures 224 and one or more target ligands 706. The prediction system 200 can include one or more or processors 216 that are able to receive computer program instructions from a general purpose computer, special purpose computer, or any other programmable data processing apparatus. The one or more processors 216 are responsible for executing the received computer program instructions, e.g., instructions provided by modules stored in memory 202. The output 228 may be visualized on one or more displays 218 that are coupled to one or more graphical user interfaces 220. For example, the three-dimensional structure of a predicted target ligand-biomolecule complex 230 can be shown on display 218 and can also be manipulated and modified by a user via graphical user interface 220.

The prediction system 200 can have a memory 202 that stores information and/or instructions. The memory 202 can store a preparation module 210 that is coupled to at least one processor 216. The preparation module 220 can be programmed to receive physical parameters, e.g., pH, temperature, and salt concentration; such parameters can be used by the preparation module 210 and can also ultimately be used by other modules, such as molecular dynamics module 502. The physical parameters can be provided by a user as input 222 to the prediction system 200. The physical parameters can inform when to make preliminary modification to the template ligand-biomolecule structure 224 and/or the target ligand 706, e.g., using the hydrogen completer 400 described below.

Figure 4:
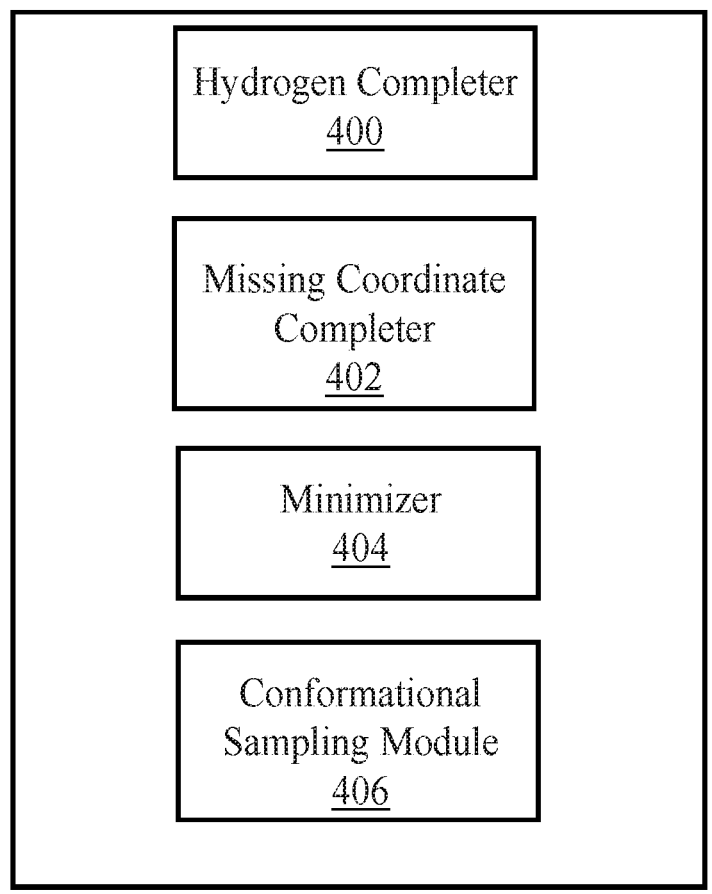
FIG. 4 is a block diagram showing one component of the prediction system shown in FIG. 2 (the preparation module).

Referring to FIG. 4, the preparation module 210 can be programmed to include a hydrogen completer 400. The hydrogen completer 410 can covalently add hydrogen atoms to appropriate locations of a template ligand-biomolecule structure 224 or target ligand 706, e.g., depending on the pH provided as user input 222. Hydrogen atom addition is also sometimes performed because experimental techniques (e.g., NMR and x-ray crystallography) are sometimes incapable of resolving all hydrogen atoms in the template ligand-biomolecule structure 224.

The preparation module 210 can also include a missing coordinate completer 402 which can be used to predict the unknown coordinates of certain atoms when the template ligand-biomolecule structure 224 is an incomplete structure, or when restoring previously mutated residues (e.g., after modification step 104 but before performing the ranking step 106) to their original residue. The template ligand-biomolecule structure 224 can be incomplete because some empirical techniques are incapable of resolving the myriad structures adopted by floppy/flexible regions of a biomolecule, and so the input 222 of the template ligand-biomolecule complex 224 may be missing atomic coordinates for certain residues. In these situations, the unresolved regions of the incomplete structure can be resolved using the missing coordinate completer 402, which can communicate with other modules, e.g., the molecule dynamics module 504 of the prediction system 200, to predict the unknown atomic coordinates.

The preparation module 210 can also include a minimizer 404 that is capable of performing energetic minimization using classical molecular mechanics forcefields. For example, the minimizer 404 can be used to energetically relax the template ligand-biomolecule structure 224 after using the hydrogen completer 410 and the missing coordinate completer 402. The minimizer 404 can also be useful when performing step 104 of the method shown in FIG. 1, where the minimizer 404 can be used to partially or completely alleviate clashes 710.

The preparation module 210 can also include a conformational sampling module 406. The conformational sampling module 406 can be used to sample other viable three-dimensional conformations of the template ligand-biomolecule complex 224, besides the conformation provided as input 222. The conformational sampling module 406 can contain or be coupled to molecular dynamics module 504, conformation explorer 502, and/or any other module capable of identifying alternative three-dimensional conformations of the template-ligand biomolecule complex 224. Such sampling can be especially useful when the template ligand-biomolecule structure 224 is known or suspected to be floppy/flexible but the experimental technique used to generate the template ligand-biomolecule structure 224 was only capable of resolving one or some of the myriad of potential structures.

Figure 3:
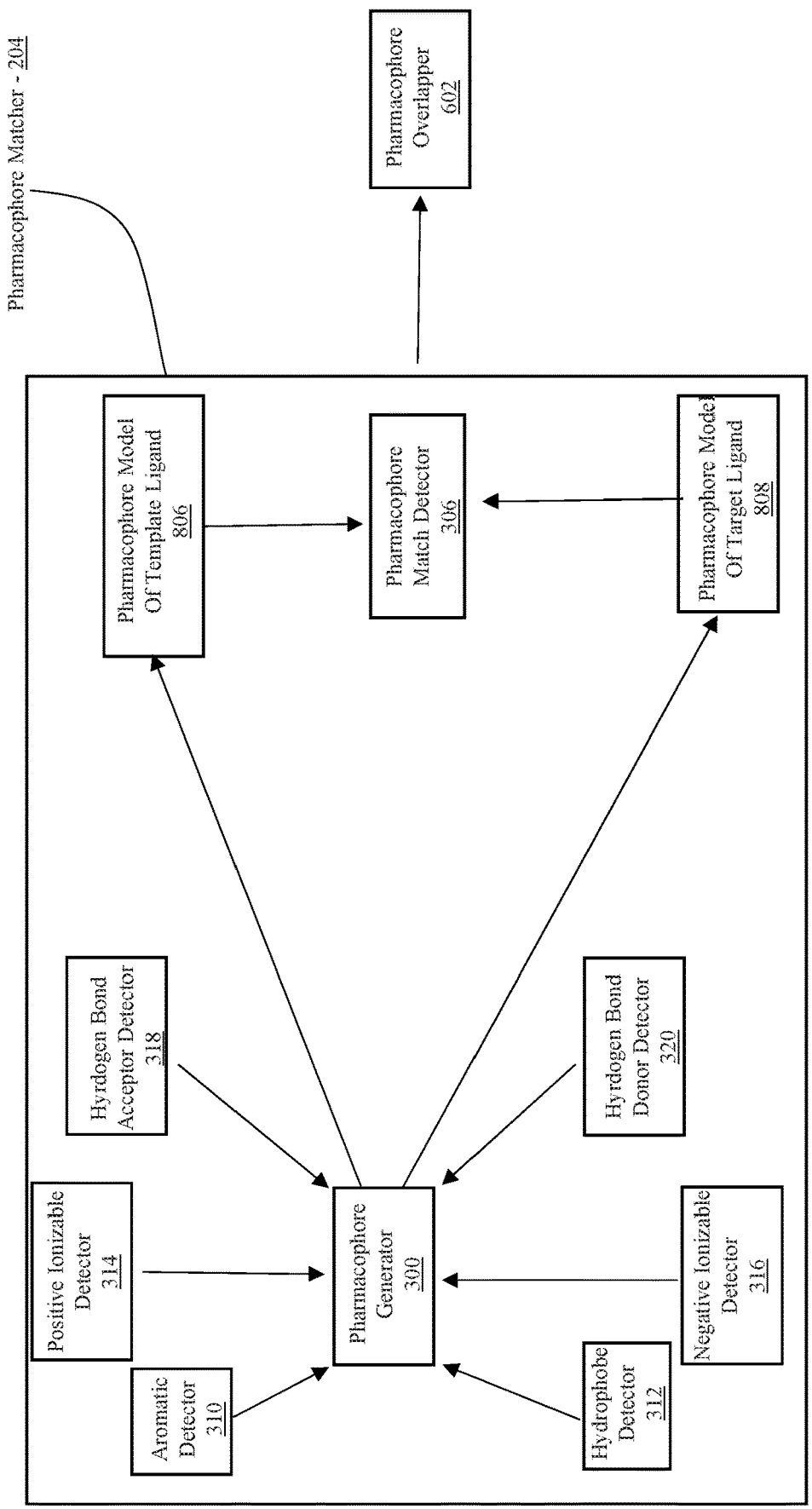
FIG. 3 is a block/flow diagram showing one component of the prediction system shown in FIG. 2 (the pharmacophore matcher module).

The memory 202 can also store a pharmacophore matcher module 204 that is coupled to at least one processor 216. The pharmacophore matcher module 204 can be programmed to generate pharmacophores for a template ligand 704 and a target ligand 706 using pharmacophore generator 300. Pharmacophore generator 300 can includes various detectors that are capable of identifying pharmacophores in a molecule; the detectors can be either default detectors pre-set in prediction system 200 or can be supplied as input 222 by a user. An aromatic detector 310 can detect pharmacophores of the aromatic group type 804. Hydrophobe detector 312 can detect pharmacophores of the hydrophobic group type 800. Positive ionizable detector 314 can detect pharmacophore groups that can become positively ionized; similarly, negative ionizable detector 316 can detect pharmacophore groups that can become negatively charged. Hydrogen bond acceptor detector 318 can detect hydrogen bond acceptor pharmacophores 802; similarly, hydrogen bond donor detector 320 can detect hydrogen bond donor pharmacophores. The pharmacophore detectors shown in FIG. 3 are only some examples of pharmacophore detectors; other types of pharmacophore detectors besides those shown in FIG. 3 can also be used, e.g., a user can define a pharmacophore as input 222.

The pharmacophore matcher module 204 can also be programmed to identify one or more pharmacophore matches 816 between the pharmacophore model 806 of template ligand 704 and the pharmacophore model 808 of the target ligand 706, using pharmacophore match detector 306. Pharmacophore match detector 306 can use any number of algorithms to detect common pharmacophores. Matches (common pharmacophores and/or superimpositions) between the pharmacophore model 806 of template ligand 704 and the pharmacophore model 808 of the target ligand 706 can be communicated to the pharmacophore overlapper 602 of the docking module 208.

The target ligand 706 that is analyzed by the pharmacophore matcher module 204 can be selected from a plurality of ligand candidates stored in a target ligand database 214, where the target ligand database can be stored in memory 202 and coupled to at least one processor 216. Selection of the target ligand 706 from target ligand database 214 can comprise comparing a pharmacophore model 806 of the template ligand 704 to a pharmacophore model of each respective one of the plurality of ligand candidates in the target ligand database 214 and choosing a ligand candidate based on the RMSD of the superimposition of the pharmacophore model of the ligand candidate and the template ligand 704 (lower RMSD would indicate a better ligand candidate). The pharmacophore matcher module 204 can be used to create pharmacophore models for each ligand candidate in the target ligand database 214, and pharmacophore match detector 306 can be used to perceive common pharmacophores and create superimposition options.

The memory 202 can also store a docking module 208 that is coupled to at least one processor 216. The docking module 208 can be programmed to predict a docked ligand position of the target ligand 706 in the template ligand-biomolecule structure 224 by overlapping the pharmacophore model 808 of the target ligand 706 with the pharmacophore model 806 of the template ligand 704 while the template ligand 704 is in the binding site 702 of the biomolecule 700 (step 102 in FIG. 1), using the pharmacophore overlapper 602.

The docking module 208 can also be programmed to predict a re-docked ligand position of the target ligand 706 in the altered biomolecule 701 (e.g., after step 104 of the method in FIG. 1 is performed to yield an altered biomolecule 701 reflecting induced fit conformational changes), using interaction optimizer 604. Instead of using pharmacophore overlap for docking, interaction optimizer 604 can predict a re-docked position of target ligand 706 by optimizing interactions between the target ligand 706 and the active site 702 of altered biomolecule 701 (e.g., optimizing hydrogen bonding interactions, salt-bridges, hydrophobic interactions, etc.). It will be understood that interaction optimizer 604 is one example of how non-pharmacophore-based docking can be accomplished—other modules in addition to interaction optimizer 604 can also be incorporated into docking module 208, each module having a different docking technique.

The memory 202 can also store a biomolecule modification module 206 that is coupled to at least one processor 216. The biomolecule modification module 206 can be programmed to achieve an induced fit effect by modifying the atomic coordinates of the biomolecule 700 to reduce clashes 710 between the docked target ligand 706 and the biomolecule 700, thereby creating an altered ligand-biomolecule structure 230 having an altered biomolecule 701 and a docked target ligand 706. Biomolecule modification module 206 can include a clash identifier 500 that can identify energetically unfavorable interactions between biomolecule 700 and target ligand 706; the regions of the biomolecule 700 that have energetically unfavorable interactions (e.g., clash 710) are the regions of the biomolecule 700 that are most likely to undergo conformational changes due to the induced fit effect.

The biomolecule modification module 206 can also include various modules that are capable of resolving energetically unfavorable interactions (e.g., clash 710). For example, minimizer 404 can alleviate clashes 710 by performing energetic minimization using classical molecular mechanics forcefields to move the specific atoms in biomolecule 700 that clash with target ligand 706 (thereby creating an altered biomolecule 701). As another example, biomolecule modification module 206 can include conformation explorer 502, which can use Monte Carlo conformational searches to explore non-clashing positions of the side-chains of biomolecule 700 (e.g., rotamer optimization). As yet another example, biomolecule modification module 206 can include molecular dynamics module 504 that can typically be used after minimizer 404 has been used; molecular dynamics module 504 can use a typical molecular mechanics forcefield to simulate the biomolecule 700 with the docked target ligand 706 in the binding site 702, thereby exploring the conformational space of biomolecule 700 when target ligand 706 is docked in its active site 702. Molecular dynamics module 706 can include various sampling techniques besides simple simulation, e.g., the replica exchange technique. As yet another example, if biomolecule 700 is a protein (or another biomolecule with sidechains), biomolecule modification module 206 can include mutator 506 that can resolve clashes 710 between target ligand 706 and specific sidechains of biomolecule 700 by computationally mutating the clashing sidechains, e.g., by truncating the clashing sidechains of biomolecule 700 to alanine (alanine is a smaller amino acid that is less likely to sterically clash with a target ligand 706), thereby yielding an altered biomolecule 701.

Figure 5:
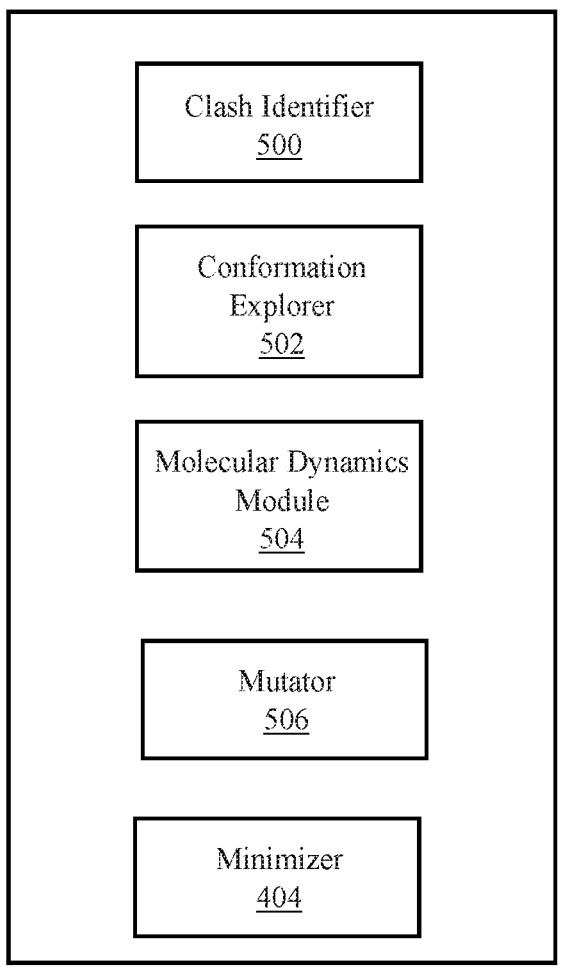
FIG. 5 is a block diagram showing one component of the prediction system shown in FIG. 2 (the biomolecule modification module).
Figure 6:
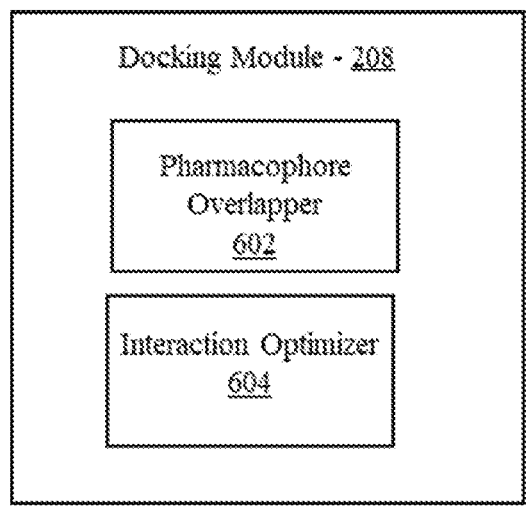
FIG. 6 is a block diagram showing one component of the prediction system shown in FIG. 2 (the docking module).

The modules shown in FIG. 5 are only some of the options for achieving an induced fit effect using biomolecule modification module 206; other modules not shown in FIG. 5 may also be included in biomolecule modification module 206. One or all of the above-mentioned modules can be used to resolve clashes 710 and ultimately achieve an induced fit effect. For example, mutator 506 may be first used, then minimizer 404, and finally molecular dynamics module 504. As another example, conformation explorer 502 may be first used, then minimizer 404, and finally molecular dynamics module 504. Mutator 506 can be used at various steps in the process, e.g., mutator 506 can be used to mutate a clashing residue to a smaller residue (e.g., alanine) during modification step 104, and mutator 506 can also be used to restore a mutated residue (e.g., alanine) to its original residue after performing modification step 104 but before performing the ranking step 106 or before repeating step 104 (after such restoration, preparation module 210 can be used to minimize and/or sample the complex 230). Ultimately, the output of the biomolecule modification module 206 can be one or more predicted structures for target ligand-biomolecule complex 230, where the target ligand-biomolecule complex 230 comprises the target ligand 706 and the altered biomolecule 701.

The memory 202 can also store a ranking module 212 that is coupled to at least one processor 216. The ranking module 212 can be programmed to receive the structure of each target ligand-biomolecule complex 230 from the biomolecule modification module 206, and rank each target ligand-biomolecule structure 230 (comprising the altered biomolecule 701 and target ligand 706) using a scoring function. The ranking module 212 can be useful in instances where (i) the target ligand 706 has more than one structural conformation and the method shown in FIG. 1 is performed on each structural conformation, and/or (ii) more than one pharmacophore model is created for the target ligand 706 or the template ligand 704, etc.

The prediction system 200 represents only one embodiment of a computer prediction system within the scope of this disclosure; other embodiments may include more or less input 222, more or less output 228, and more or less modules and components within the software and hardware of the prediction system. In addition, it will be understood that while FIG. 2 shows individual separate modules, any of the shown modules could in fact be a sub-module of any of the other shown modules. For example, as previously described, the molecular dynamics module 504 could be part of or coupled to the preparation module 210. Similarly, the minimizer 404 can be part of or coupled to the molecule dynamics module 504. As another example, the preparation module 210 could be a sub-module of the biomolecule modification module 206, and vice-versa.

Figure 11:
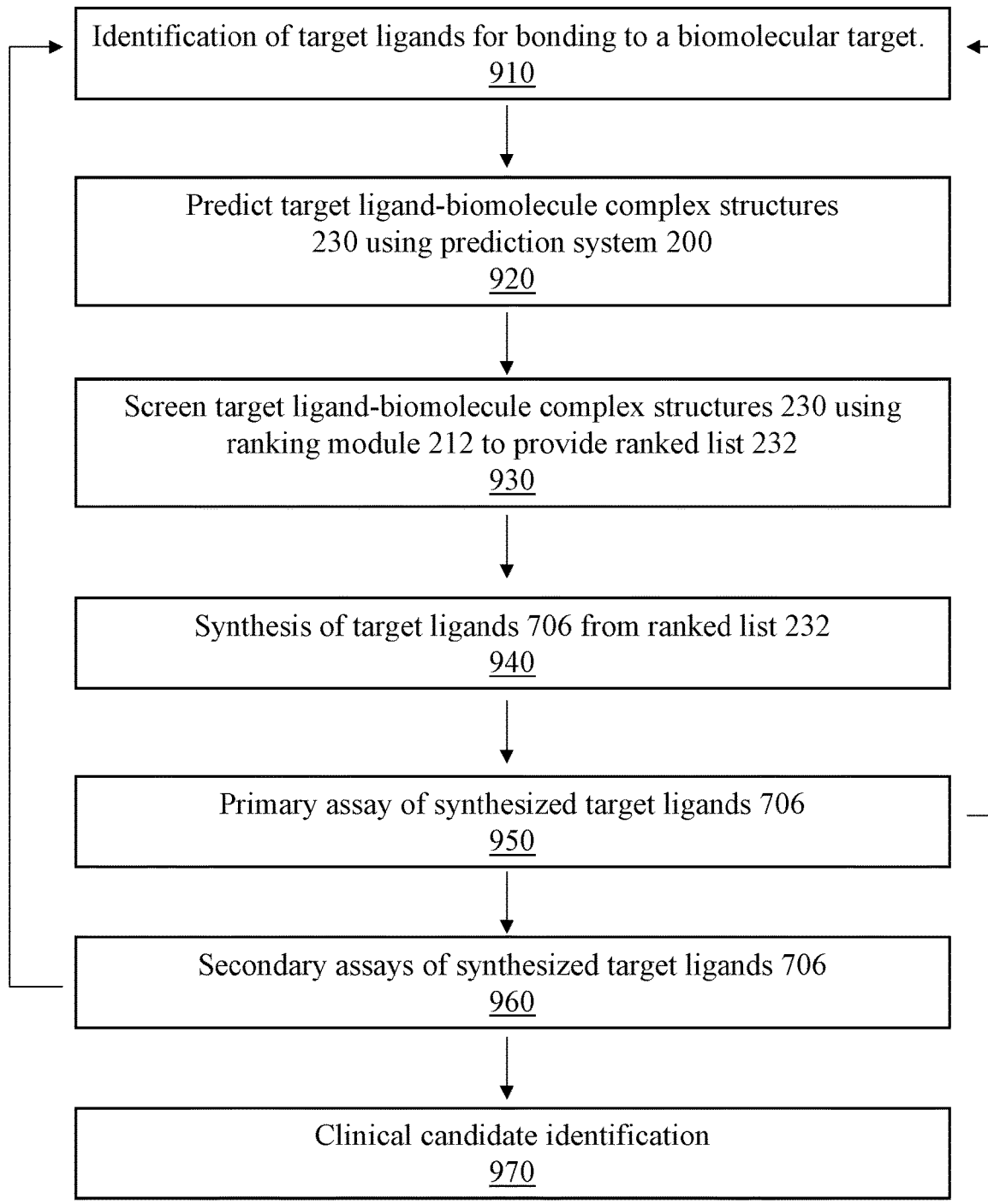
FIG. 11 is a flow chart illustrating steps in an exemplary drug design method that includes induced fit docking computations.

In some embodiments, the induced fit docking calculations can be used to evaluate compounds in drug discovery. For example, the computational approaches described above can be used as a virtual filter for screening compounds for their suitability as a candidate for new pharmaceutical applications. Referring to FIG. 11, an exemplary drug design protocol 1101 that incorporates these computational approaches is illustrated as a flow chart. Here, the process begins by identifying one or more target ligands 706 for bonding to a biomolecular target 700 (step 910). Typically, the biomolecular target 700 is a protein, nucleic acid, or some other biological macromolecule involved in a particular metabolic or signaling pathway associated with a specific disease condition or pathology or to the infectivity or survival of a microbial pathogen. In some cases, the target ligands 706 are selected small molecules that are complementary to a binding site of the target. Examples of target ligands 706 can be molecules that are expected to serve as: receptor agonists, antagonists, inverse agonists, or modulators; enzyme activators or inhibitors; or ion channel openers or blockers. In some studies, a large number of target ligands 706 (e.g., hundreds or thousands) are identified.

Once target ligands 706 are identified, prediction system 200 can be used to predict target ligand-biomolecule complex structures 230 using generally the techniques described above, e.g., inter alia, using pharmacophore matcher 204 and docking module 208 (step 920). Generally, the prediction calculated described above may be performed across a computer network. For example, the calculations may be performed using one or more servers that a researcher accesses via a network, such as the internet.

The predicted target ligand-biomolecule complex structures 230 are then screened (step 930), e.g. using ranking module 212 to provide a ranked list 232, in order to identify candidates for chemical analysis, which involves first synthesizing the target ligands 706 (step 940) and then assaying the synthesized target ligands 706 (steps 950 and 960). Screening molecules can be performed as described above in step 108, e.g. by using a scoring function.

Synthesis typically includes several steps including choosing a reaction pathway to make the compound, carrying out the reaction or reactions using suitable apparatus, separating the reaction product from the reaction mixture, and purifying the reaction product. Chemical composition and purity can be checked to ensure the correct compounds are assayed.

Generally, multiple different assays can be performed on each target ligand 706. For example, in step 950, primary assays can be performed from on all synthesized target ligands 706 (step 960). The primary assays can be high throughput assays that provide a further screen for the target ligands 706 rather that performing every necessary assay on every target ligand 706 selected from the computational screening step. Secondary assays (step 960) are performed on those molecules that demonstrate favorable results from the primary assays. Secondary assays can include both in vitro or in vivo assays to assess, e.g., selectivity and/or liability. Both the primary and secondary assays can provide information useful for identifying additional target ligands 706 for further computational screening.

Target ligands 706 with favorable results from the secondary assays can be identified as suitable candidates for further preclinical evaluation (step 970).

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory program carrier for execution by, or to control the operation of, a data processing apparatus. Alternatively, or in addition, the program instructions can be encoded on an artificially-generated propagated signal, e.g., a machine-generated electrical, optical, or electromagnetic signal, that is generated to encode information for transmission to a suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable processor, a computer, or multiple processors or computers. The apparatus can also be or further include special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Computers suitable for the execution of a computer program include, by way of example, general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) or LED (light emitting diode) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface or a Web browser through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the user device, which acts as a client. Data generated at the user device, e.g., a result of the user interaction, can be received from the user device at the server.

Figure 12:
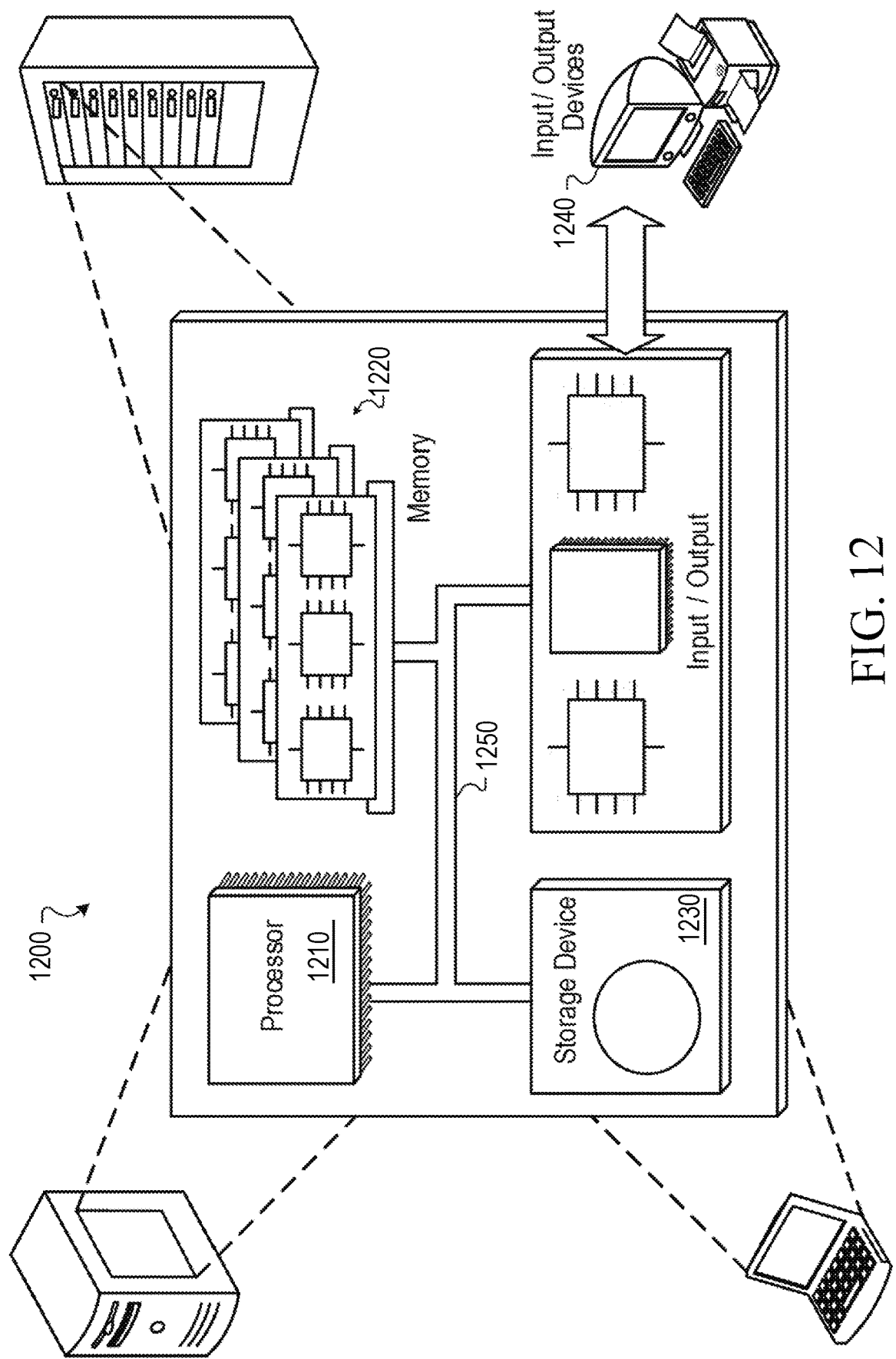
FIG. 12 is a diagram of a computer system.

An example of one such type of computer is shown in FIG. 12, which shows a schematic diagram of a generic computer system 1200. The system 1200 can be used for the operations described in association with any of the computer-implemented methods described previously, according to one implementation. The system 1200 includes a processor 1210, a memory 1120, a storage device 1230, and an input/output device 1240. Each of the components 1210, 1120, 1230, and 1240 are interconnected using a system bus 1250. The processor 1210 is capable of processing instructions for execution within the system 1200. In one implementation, the processor 1210 is a single-threaded processor. In another implementation, the processor 1210 is a multi-threaded processor. The processor 1210 is capable of processing instructions stored in the memory 1120 or on the storage device 1230 to display graphical information for a user interface on the input/output device 1240.

The memory 1120 stores information within the system 1200. In one implementation, the memory 1120 is a computer-readable medium. In one implementation, the memory 1120 is a volatile memory unit. In another implementation, the memory 1120 is a non-volatile memory unit.

The storage device 1230 is capable of providing mass storage for the system 1200. In one implementation, the storage device 1230 is a computer-readable medium. In various different implementations, the storage device 1230 may be a floppy disk device, a hard disk device, an optical disk device, or a tape device.

The input/output device 1240 provides input/output operations for the system 1200. In one implementation, the input/output device 1240 includes a keyboard and/or pointing device. In another implementation, the input/output device 1240 includes a display unit for displaying graphical user interfaces.

While this specification contains many specific implementation details, these should not be construed as limitations on the scope of what may be claimed, but rather as descriptions of features that may be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

What is claimed is:

1. A method for predicting a docked position of a target ligand in a binding site of a biomolecule, the method comprising:
   receiving a template ligand-biomolecule structure, the template ligand-biomolecule structure comprising a template ligand docked in the binding site of the biomolecule;
   comparing a pharmacophore model of the template ligand to a pharmacophore model of the target ligand;
   overlapping the pharmacophore model of the target ligand with the pharmacophore model of the template ligand while the template ligand is in the binding site of the biomolecule;
   predicting the docked position of the target ligand in the binding site of the biomolecule based on a position of the pharmacophore model of the target ligand when overlapped with the pharmacophore model of the template ligand;
   selecting the target ligand from among a plurality of possible target ligands based on the predicted docked position; and
   synthesizing the target ligand.

2. The method of claim 1, further comprising selecting the target ligand from a plurality of ligand candidates, each of the ligand candidates being different from the template ligand, and wherein selecting the target ligand comprises comparing the pharmacophore model of the template ligand to a pharmacophore model of each respective one of the plurality of ligand candidates.

3. The method of claim 1, further comprising receiving a plurality of template ligand-biomolecule structures, each template ligand-biomolecule structure having a different template ligand docked in the binding site of the biomolecule, and generating the pharmacophore model of the template ligand by combining information from each of the template ligands from the plurality of template ligand-biomolecule structures.

4. The method of claim 1, wherein the target ligand has more than one structural conformation in its unbound state, and the docked position of the target ligand in the binding site of the biomolecule is predicted by enumerating a set of potential target ligand conformations and overlapping a respective pharmacophore model of the target ligand for each of the potential target ligand conformations with the pharmacophore model of the template ligand while the template ligand is in the binding site of the biomolecule.

5. The method of claim 4, wherein predicting the docked position of the target ligand in the binding site of the biomolecule comprises ignoring at least one clash between the target ligand conformations' atomic coordinates and the biomolecule's atomic coordinates.

6. The method of claim 5, further comprising, for each target ligand conformation, modifying atomic coordinates of the biomolecule to reduce clashes between the docked target ligand conformations' atomic coordinates and the biomolecule's atomic coordinates, thereby creating an altered ligand-biomolecule structure comprising the docked target ligand and an altered biomolecule.

7. The method of claim 6, further comprising, predicting a re-docked position of each target ligand conformation by predicting each target ligand conformation's position in the binding site of the altered biomolecule; and
   for each target ligand conformation, modifying atomic coordinates of the altered biomolecule to reduce clashes between the atomic coordinates of the target ligand conformation's re-docked position and the atomic coordinates of the altered biomolecule, thereby creating a re-altered ligand-biomolecule structure comprising a re-docked target ligand and a re-altered biomolecule.

8. The method of claim 7, further comprising ranking each altered and re-altered ligand-biomolecule structure using a scoring function.

9. The method of claim 8, further comprising identifying a subset of high-ranking target ligands corresponding to target ligands having a threshold value for an empirical activity.

10. The method of claim 1, further comprising compiling a ranked list of target ligands that includes the target ligand based on the predicted dock position and synthesizing one or more target ligands from the ranked list.

11. The method of claim 10, further comprising performing at least one assay of the one or more synthesized target ligands.

12. The method of claim 11, further comprising identifying a clinical candidate from the ranked list of target ligands based on the at least one assay.

13. The method of claim 4, wherein predicting the docked position of the target ligand in the binding site of the biomolecule comprises determining at least one clash between the target ligand conformations' atomic coordinates and the biomolecule's atomic coordinates results in interactions requiring modifications of the biomolecule exceeding a pre-set criteria; and providing an alert that the target ligand is not suitable.

14. The method of claim 13, wherein the clash comprises a clash between an atom of the target ligand and a backbone atom of the biomolecule.

15. The method of claim 5, wherein modifying atomic coordinates of the biomolecule to reduce clashes between the docked target ligand conformations' atomic coordinates and the biomolecule's atomic coordinates comprises computationally mutating clashing sidechains of the biomolecule.

\* \* \* \* \*